(12) United States Patent
Giles et al.

(10) Patent No.: US 9,947,518 B2
(45) Date of Patent: Apr. 17, 2018

(54) COMBINED TANDEM MASS SPECTROMETRY AND ION MOBILITY MASS SPECTROMETRY

(71) Applicant: MICROMASS UK LIMITED, Wilmslow (GB)

(72) Inventors: Kevin Giles, Stockport (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/312,399

(22) PCT Filed: May 29, 2015

(86) PCT No.: PCT/GB2015/051568
§ 371 (c)(1),
(2) Date: Nov. 18, 2016

(87) PCT Pub. No.: WO2015/181563
PCT Pub. Date: Dec. 3, 2015

(65) Prior Publication Data
US 2017/0110303 A1    Apr. 20, 2017

(30) Foreign Application Priority Data

May 30, 2014  (EP) .................................... 14170528
May 30, 2014  (GB) .................................. 1409578.0

(51) Int. Cl.
*H01J 49/00*   (2006.01)
*G01N 27/62*   (2006.01)

(52) U.S. Cl.
CPC ........ *H01J 49/0031* (2013.01); *G01N 27/622* (2013.01); *H01J 49/0045* (2013.01)

(58) Field of Classification Search
CPC . H01J 49/0031; H01J 49/0045; G01N 27/622
(Continued)

(56) References Cited

U.S. PATENT DOCUMENTS

| 7,586,088 B2 | 9/2009 | Bateman et al. |
| 8,530,831 B1 | 9/2013 | Coon et al. |

(Continued)

FOREIGN PATENT DOCUMENTS

WO    WO 2013140132 A2 *  9/2013  ............ H01J 49/004

*Primary Examiner* — Michael Maskell

(57) ABSTRACT

A method of analyzing ions is disclosed comprising performing an initial multi-dimensional survey scan comprising separating parent ions according to a first physico-chemical property and separating the parent ions according to a second physico-chemical property. At least one parent ion of interest from the initial multi-dimensional survey scan is determined, the at least one parent ion of interest having a first value or range of the first physico-chemical property and a second value or range of the second physico-chemical property. Then, during a subsequent single cycle of separation, the method further comprises separating parent ions according to the first physico-chemical property. If the parent ions have a value or range of the first physico-chemical property which corresponds with the first value or range, then the method further comprises selecting parent ions of interest having a value or range of the first physico-chemical property which corresponds with the first value or range and which also have a value or range of the second physico-chemical property which corresponds with the second value or range. If the parent ions have a value or range of the first physico-chemical property which does not correspond with the first value or range then the method further comprises separating the parent ions according to the first physico-chemical property and separating the parent ions according to the second physico-chemical property.

20 Claims, 2 Drawing Sheets

(58) Field of Classification Search
USPC .................................................. 250/281, 282
See application file for complete search history.

(56) References Cited

U.S. PATENT DOCUMENTS

| | | |
|---|---|---|
| 9,123,523 B2 | 9/2015 | Green et al. |
| 9,190,251 B2 | 11/2015 | Green et al. |
| 9,460,902 B2 | 10/2016 | Wildgoose |
| 9,576,777 B2 * | 2/2017 | Giles .................... H01J 49/004 |
| 2013/0289894 A1 | 10/2013 | Cox et al. |
| 2015/0041636 A1 | 2/2015 | Giles et al. |

* cited by examiner

COMBINED TANDEM MASS SPECTROMETRY AND ION MOBILITY MASS SPECTROMETRY

CROSS-REFERENCE TO RELATED APPLICATIONS

This application represents the U.S. National Phase of International Application No. PCT/GB2015/051568 entitled "Combined Tandem Mass Spectrometry and Ion Mobility Mass Spectrometry" filed 29 May 2015, which claims priority from and the benefit of United Kingdom patent application No. 1409578.0 filed on 30 May 2014 and European patent application No. 14170528.5 filed on 30 May 2014. The entire contents of these applications are incorporated herein by reference.

FIELD OF THE INVENTION

The present invention relates generally to mass spectrometry and in particular to methods of analysing ions, methods of mass spectrometry, analytical instruments for analysing ions and mass spectrometers.

BACKGROUND

It is known to perform Data Dependent Acquisitions ("DDA") using a mass spectrometer wherein an initial survey scan of parent ions is performed. Once an initial survey scan has been performed, parent ions of interest are determined and are then isolated or selected by a quadrupole mass filter. The parent ions of interest are isolated or selected by arranging for the mass filter to transmit just the specific parent ions of interest on the basis of the mass to charge ratio of the parent ions. The parent ions of interest may then be fragmented and the resulting fragment ions may then be mass analysed. Mass analysis of the resulting fragment ions enables the parent ions of interest to be identified or the identity of the parent ions of interest to be confirmed.

However, this known approach suffers from the problem of having a relatively low duty cycle since a plurality of species of parent ions will arrive at the quadrupole mass filter at substantially the same time but only a single species of parent ions of interest will be onwardly transmitted by the mass filter. The other parent ions of interest will be attenuated by the mass filter.

The known approach also exhibits insufficient selectivity of the isolation step when processing complex mixtures. For example, two different species of parent ions may have substantially the same mass to charge ratio but the quadrupole mass filter will transmit both species of parent ions since the mass filter is unable to distinguish between the two different species of parent ions.

An improvement to the known approach is described in WO 2013/140132 (Micromass) which discloses an approach wherein an initial multi-dimensional survey scan is performed comprising separating parent ions according to a first physico-chemical property (e.g. ion mobility) and then separating the parent ions according to a second physico-chemical property (e.g. mass to charge ratio). A plurality of parent ions of interest are then determined from the initial multi-dimensional survey scan. The plurality of parent ions of interest are then sequentially selected based upon the first and second physico-chemical properties during a single cycle of separation. The parent ions of interest may then be fragmented and corresponding fragment ions may then be mass analysed.

The multi-dimensional separation of the ions results in improved specificity of the precursor or parent ions (or resulting fragment ions), improved isolation and significantly improved duty cycle compared the known approach as described above.

However, during the single acquisition or cycle of separation after the initial multi-dimensional survey scan, the system is operated continuously in a selective (narrow-band) mode of operation (at sequential different values of the second physico-chemical property) so that for regions of the data where no parent ions of interest are present, ions will be lost to the system and no useful data will be acquired.

It is therefore desired to provide an improved mass spectrometer and an improved method of mass spectrometry.

SUMMARY

According to an aspect there is provided a method of analysing ions comprising:

performing an initial multi-dimensional survey scan comprising separating parent ions according to a first physico-chemical property and separating the parent ions according to a second physico-chemical property;

determining at least one parent ion of interest from the initial multi-dimensional survey scan, the at least one parent ion of interest having a first value or range of the first physico-chemical property and a second value or range of the second physico-chemical property;

and then during a subsequent single cycle of separation:

(i) separating parent ions according to the first physico-chemical property;

wherein if the parent ions have a value or range of the first physico-chemical property which corresponds with the first value or range, then the method further comprises selecting parent ions of interest having a value or range of the first physico-chemical property which corresponds with the first value or range and which also have a value or range of the second physico-chemical property which corresponds with the second value or range; and wherein if the parent ions have a value or range of the first physico-chemical property which does not correspond with the first value or range then the method further comprises separating the parent ions according to the first physico-chemical property and separating the parent ions according to the second physico-chemical property.

Various embodiments represent an improvement over the approach described in WO 2013/140132 (Micromass). According to the known approach, a plurality of parent ions of interest are sequentially selected based upon first (e.g. ion mobility) and second (e.g. mass to charge ratio) physico-chemical properties during a single cycle of separation e.g. by sequentially switching a mass filter so as to selectively transmit parent ions having mass to charge ratios of interest during the cycle time of the ion mobility spectrometer.

According to various embodiments the system may be configured so as to select parent ions of interest based upon the first and second physico-chemical properties in a corresponding manner, but to additionally operate in (e.g. switch to) a non-selective (e.g. wide-band) transmission mode of operation for regions of the data where no parent ions of interest are present.

For example, in embodiments where the first physico-chemical property comprises ion mobility and the second physico-chemical property comprises mass to charge ratio, the approach may involve switching a mass filter at the appropriate time to a filtering mode of operation so as to selectively transmit parent ions of interest having a particular ion mobility drift time and mass to charge ratio, and then additionally switching the mass filter to a wide-band, non-selective mode of operation at other times (e.g. in-between the times of interest) when no parent ions of interest are present.

Thus, according to an embodiment, in the single acquisition or cycle of separation after the initial multi-dimensional survey scan has been performed, for regions of the data where no parent ions of interest are present (as determined by the initial multi-dimensional survey scan), the system may be operated in a mode of operation wherein further multi-dimensional survey scan-type (e.g. non-selective wide-band) data is acquired. It will be appreciated that such an approach according to an embodiment is in contrast to the approach described in WO 2013/140132 (Micromass), wherein in the single acquisition or cycle of separation after the initial multi-dimensional survey scan, the system is operated continuously in a selective (narrow-band) mode of operation (at sequential different values of the second physico-chemical property) so that for regions of the data where no parent ions of interest are present, ions will be lost to the system and no useful data will be acquired.

Thus, according to various embodiments, additional useful (e.g. multi-dimensional survey scan-type) data is acquired for regions of the data where no parent ions of interest are determined to be present (i.e. from the initial multi-dimensional survey scan). This additional data is not acquired using the method of WO 2013/140132 (Micromass). Accordingly, embodiments advantageously allow more useful data to be acquired during a single experimental acquisition or cycle, in the same amount of time and using the same amount of sample. Furthermore, the overall duty-cycle of the system is increased.

According to an embodiment, the first physico-chemical property comprises ion mobility, differential ion mobility, mass, mass to charge ratio or time of flight.

According to an embodiment, the second physico-chemical property comprises ion mobility, differential ion mobility, mass, mass to charge ratio or time of flight.

According to an embodiment, separating ions according to the first physico-chemical property comprises separating ions temporally.

According to an embodiment, separating ions according to the second physico-chemical property comprises separating ions temporally.

According to an embodiment, separating ions according to the first physico-chemical property comprises separating ions spatially.

According to an embodiment, separating ions according to the second physico-chemical property comprises separating ions spatially.

The method may further comprise using an ion mobility or differential ion mobility separator to separate the parent ions according to their ion mobility or differential ion mobility.

The method may further comprise using a time of flight mass analyser, an ion trap, or a scanning mass to charge ratio filter to separate the parent ions according to their mass, mass to charge ratio or time of flight.

The method may further comprise using a quadrupole rod set mass filter or a notched broadband quadrupolar frequency to filter the parent ions according to their mass, mass to charge ratio or time of flight.

The method may further comprise causing the selected parent ions of interest to fragment or react so as to form fragment or product ions.

According to an embodiment, the first physico-chemical property and the second physico-chemical property are the same and/or are substantially correlated.

According to an embodiment, the first physico-chemical property and the second physico-chemical property are substantially different and/or are substantially uncorrelated.

According to an embodiment, the method comprises:

determining at least a first parent ion of interest and a second parent ion of interest from the initial multi-dimensional survey scan, the first parent ion of interest having a first value or range of the first physico-chemical property and a second value or range of the second physico-chemical property, the second parent ion of interest having a third value or range of the first physico-chemical property and a fourth value or range of the second physico-chemical property;

and then during the subsequent single cycle of separation:

(i) separating parent ions according to the first physico-chemical property;

wherein if the parent ions have a value or range of the first physico-chemical property which corresponds with the first value or range, then the method further comprises selecting parent ions of interest having a value or range of the first physico-chemical property which corresponds with the first value or range and which also have a value or range of the second physico-chemical property which corresponds with the second value or range;

wherein if the parent ions have a value or range of the first physico-chemical property which corresponds with the third value or range, then the method further comprises selecting parent ions of interest having a value or range of the first physico-chemical property which corresponds with the third value or range and which also have a value or range of the second physico-chemical property which corresponds with the fourth value or range; and wherein if the parent ions have a value or range of the first physico-chemical property which does not correspond with the first and/or third value or range then the method further comprises separating the parent ions according to the first physico-chemical property and separating the parent ions according to the second physico-chemical property.

According to an embodiment, the method comprises:

determining one or more third parent ions of interest from the initial multi-dimensional survey scan, the one or more third parent ions of interest having one or more fifth values or ranges of the first physico-chemical property and one or more sixth values or ranges of the second physico-chemical property;

and then during the subsequent single cycle of separation:

(i) separating parent ions according to the first physico-chemical property;

wherein if the parent ions have a value or range of the first physico-chemical property which corresponds with the one or more fifth values or ranges, then the method further comprises selecting parent ions of interest having a value or range of the first physico-chemical property which corresponds with the one or more fifth values or ranges and which also have a value or range of the second physico-chemical property which corresponds with the one or more sixth values or ranges;

wherein if the parent ions have a value or range of the first physico-chemical property which does not correspond with the first and/or third and/or fifth values or ranges then the method further comprises separating the parent ions according to the first physico-chemical property and separating the parent ions according to the second physico-chemical property.

According to an embodiment, the initial multi-dimensional survey scan comprises analysing the parent ions.

According to an embodiment, the method comprises analysing the selected parent ions, ions derived from the selected parent ions, and/or fragment or product ions formed by fragmenting or reacting the selected parent ions.

According to an embodiment, the method comprises analysing the selected parent ions, ions derived from the selected parent ions, and/or fragment or product ions formed by fragmenting or reacting the selected parent ions, and generating a single mass spectrum for the analysed selected parent ions, ions derived from the selected parent ions, and/or fragment or product ions.

According to an embodiment, the method comprises analysing the parents ions having a value or range of the first physico-chemical property which does not correspond with the first value or range or ions derived therefrom.

According to another aspect, there is provided an analytical instrument for analysing ions comprising:

a first separator for separating ions according to a first physico-chemical property;

a second separator for separating ions according to a second physico-chemical property; and a control system arranged and adapted:

(i) to perform an initial multi-dimensional survey scan comprising separating parent ions according to the first physico-chemical property using the first separator and separating the parent ions according to the second physico-chemical property using the second separator;

(ii) to determine at least one parent ion of interest from the initial multi-dimensional survey scan, the at least one parent ion of interest having a first value or range of the first physico-chemical property and a second value or range of the second physico-chemical property;

and then during a single cycle of separation:

(iii) to cause the first separator to separate parent ions according to the first physico-chemical property;

(iv) if the parent ions have a value or range of the first physico-chemical property which corresponds with the first value or range, to select parent ions of interest having a value or range of the first physico-chemical property which corresponds with the first value or range and which also have a value or range of the second physico-chemical property which corresponds with the second value or range; and (v) if the parent ions have a value or range of the first physico-chemical property which does not correspond with the first value or range, to separate the parent ions according to the first physico-chemical property and to separate the parent ions according to the second physico-chemical property.

According to an embodiment, the analytical instrument further comprises an analyser for analysing the parent ions or ions derived from the parent ions.

According to another aspect there is provided a method of analysing ions comprising:

performing an initial multi-dimensional survey scan comprising separating parent ions according to a first physico-chemical property and separating the parent ions according to a second physico-chemical property;

determining at least one parent ion of interest from the initial multi-dimensional survey scan, the at least one parent ion of interest having a first value or range of the first physico-chemical property and a second value or range of the second physico-chemical property; and then separating parent ions according to the first physico-chemical property in a single cycle of separation, and during the single cycle of separation:

fragmenting or reacting parent ions having a value or range of the first physico-chemical property corresponding to the first value or range and having a value or range of the second physico-chemical property corresponding to the second value or range of the second physico-chemical property so as to form fragment or product ions, and analysing the fragment or product ions; and analysing second parent ions having a value or range of the first physico-chemical property that does not correspond with the first value or range.

According to another aspect there is provided an analytical instrument for analysing ions comprising:

a separator for separating ions according to a first physico-chemical property;

a fragmentation, reaction or collision device for fragmenting or reacting ions;

an analyser; and a control system arranged and adapted:

(i) to perform an initial multi-dimensional survey scan comprising separating parent ions according to a first physico-chemical property using the separator and separating the parent ions according to a second physico-chemical property;

(ii) to determine at least one parent ion of interest from the initial multi-dimensional survey scan, the at least one parent ion of interest having a first value or range of the first physico-chemical property and a second value or range of the second physico-chemical property; and then (iii) to cause the separator to separate parent ions according to the first physico-chemical property in a single cycle of separation, and during the single cycle of separation:

(iv) to cause the fragmentation, reaction or collision device to fragment or react parent ions having a value or range of the first physico-chemical property corresponding to the first value or range and having a value or range of the second physico-chemical property corresponding to the second value or range so as to form fragment or product ions, and to cause the analyser to analyse the fragment or product ions; and (v) to cause the analyser to analyse parent ions having a value or range of the first physico-chemical property that does not correspond to the first value or range.

According to another aspect there is provided a method of analysing ions comprising:

separating ions according to a first physico-chemical property in a single cycle of separation, and during the single cycle of separation:

operating a device for selecting ions according to a second physico-chemical property in a first mode of operation in which the ions are selected according to the second physico-chemical property; and operating the device in a second mode of operation in which the ions are not selected according to the second physico-chemical property.

According to another aspect there is provided an analytical instrument for analysing ions comprising:

a separator for separating ions according to a first physico-chemical property;

a device for selecting ions according to a second physico-chemical property; and a control system arranged and adapted:

to cause the separator to separate ions according to the first physico-chemical property in a single cycle of separation; and during the single cycle of separation, to operate the device in a first mode of operation in which the ions are selected according to the second physico-chemical property, and to operate the device in a second mode of operation in which the ions are not selected according to the second physico-chemical property.

According to another aspect there is provided a method of analysing ions comprising:

separating ions according to a first physico-chemical property in a single cycle of separation, and during the single cycle of separation:

fragmenting or reacting the ions having a first value or range of the first physico-chemical property and a first value or range of the second physico-chemical property so as to form fragment or product ions, and analysing the fragment or product ions; and analysing the ions having a second value or range of the first physico-chemical property.

According to another aspect there is provided an analytical instrument for analysing ions comprising:

a separator for separating ions according to a first physico-chemical property;

a fragmentation, reaction or collision device for fragmenting or reacting ions; and a control system arranged and adapted:

(i) to cause the separator to separate ions according to the first physico-chemical property in a single cycle of separation; and during the single cycle of separation of the separator:

(ii) to cause the fragmentation, reaction or collision device to fragment or react the ions having a first value or range of the first physico-chemical property and a first value or range of the second physico-chemical property so as to form fragment or product ions, and to cause the analyser to analyse the fragment or product ions; and (iii) to cause the analyser to analyse the ions having a second value or range of the first physico-chemical property.

According to another aspect there is provided a method of mass spectrometry comprising a method of analysing ions as described above.

According to another aspect there is provided a mass spectrometer comprising an analytical instrument as described above.

According to another aspect there is provided an apparatus for ion mobility-mass spectrometry comprising:

an ion mobility spectrometer or separator ("IMS") device arranged upstream of a mass to charge ratio ("m/z") filter and mass analyser wherein the mass to charge ratio filter is arranged to switch between a wide band transmission mode and a mass to charge ratio filtering mode within an ion mobility separation (IMS) cycle.

The switching may be driven by a survey scan.

The switch may occur more than once within an ion mobility separation (IMS) cycle.

According to an embodiment different mass to charge ratio (m/z)-drift time ("DT") regions associated with the switches are stored as separate spectra.

According to an embodiment multiple mass to charge ratio (m/z)-drift time ("DT") experiments may be combined for the same precursor or parent ions.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser;

(iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms;

(v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenan-threne; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Figure 1:
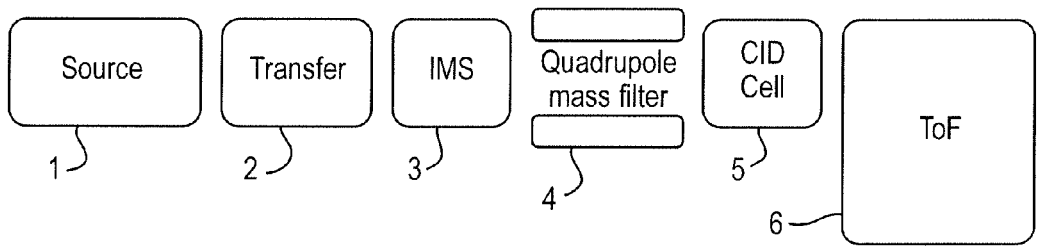
FIG. 1 shows a mass spectrometer according to an embodiment wherein an ion mobility separator is arranged upstream of a quadrupole mass filter and wherein a Time of Flight mass analyser is arranged downstream of the quadrupole mass filter.

A known approach as described in WO 2013/140132 (Micromass) will first be described.

According to the known approach an initial multi-dimensional survey scan is performed comprising separating parents ions according to a first physico-chemical property (e.g. ion mobility) and then separating the parent ions according to a second physico-chemical property (e.g. mass to charge ratio). A plurality of parent ions of interest are then determined from the initial multi-dimensional survey scan. The plurality of parent ions of interest are then sequentially selected based upon the first and second physico-chemical properties during a single cycle of separation. The parent ions of interest which are selected may then be fragmented and corresponding fragment or product ions may then be mass analysed.

Thus, the known approach essentially consists of an initial multi-dimensional survey scan, followed by ion mobility spectrometry (IMS)-tandem mass spectrometry (MS/MS) experiments on identified parent or precursor ions of interest.

In the IMS-MS/MS experiments, a plurality of parent ions of interest are sequentially selected based upon the first (e.g. ion mobility) and second (e.g. mass to charge ratio) physico-chemical properties during a single cycle of separation. The system is operated continuously in a selective (narrow-band) mode of operation at sequential different values of the second physico-chemical property (e.g. mass to charge ratio).

In one implementation of the MS/MS experiments, a mass filtering quadrupole may be switched to isolate one or more precursor ions within a single ion mobility spectrometry (IMS) cycle time. The data in the time selected regions associated with MS/MS experiments is retained with the fragment ion mass to charge ratio values and intensities used in the common workflows associated with MS/MS.

The multi-dimensional separation of the ions results in improved specificity of the precursor or parent ions (or resulting fragment or product ions), improved isolation and significantly improved duty cycle compared to other known approaches as described above.

However, in some instances there may only be one or a small number of parent or precursor ions of interest. In these instances, one or more regions of the separation space may not be identified from the survey scan for isolation in the subsequent MS/MS experiments. Accordingly, in the subsequent experiments, no data will be acquired for these regions of the data and ions will be lost to the system.

An embodiment will now be described in more detail.

Various embodiments relate to a method of operating an ion mobility enabled mass spectrometer in which regions of the two-dimensional (e.g. IMS-MS) space are selected e.g. in time and/or mass to charge ratio for MS/MS experiments whilst other regions of the data may be retained and may be used as further survey or archive data.

According to various embodiments a mass filter, such as a quadrupole mass filter, may be operated in a wide-band transmission, non-selective or non-resolving mode at IMS drift times when the system is not operating in MS/MS mode. This means that IMS-MS or survey data can be acquired during the rest of the drift time.

FIG. 1 shows a mass spectrometer according to an embodiment. An ion separator which may comprise an ion mobility spectrometer or separator ("IMS") device 3 may be arranged downstream of an ion source 1. An optional transfer component 2 may be arranged between the ion source 1 and the ion separator 3.

An ion filter, optionally a quadrupole mass filter 4, may be provided downstream of the ion separator 3. An ion analyser, optionally comprising a Time of Flight ("ToF") mass analyser 6, may be provided downstream of the ion filter 4. An optional fragmentation, reaction or collision device such as a Collision Induced Dissociation ("CID") cell 5 may be provided between the mass filter 4 and the mass analyser 6.

Figure 2:
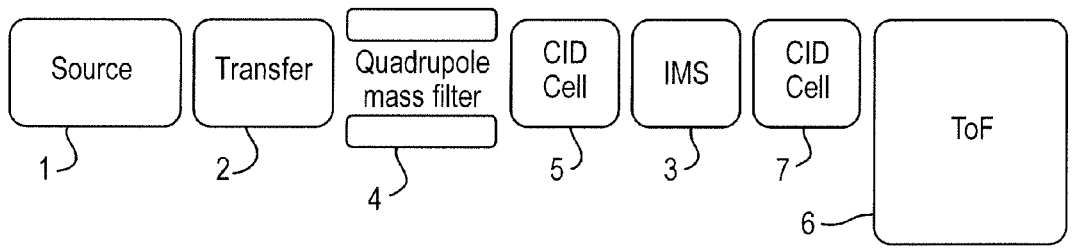
FIG. 2 shows a mass spectrometer according to another embodiment wherein a quadrupole mass filter is arranged upstream of an ion mobility separator and wherein a Time of Flight mass analyser is arranged downstream of the quadrupole mass filter.

FIG. 2 shows an alternative embodiment. An ion filter, optionally a quadrupole mass filter 4, may be provided downstream of an ion source 1. An optional transfer component 2 may be provided between the ion source 1 and the mass filter 4. An ion separator, optionally comprising an ion mobility spectrometer or separator 3, may be provided downstream of the filter 4. An analyser, optionally comprising a Time of Flight mass analyser 6, may be provided downstream of the separator 3. One or more optional fragmentation, reaction or collision devices such as Collision Induced Dissociation ("CID") cells 5,7 may be provided between the filter 4 and the separator 3 and/or between the separator 3 and the analyser 6.

It should be noted that FIGS. 1 and 2 are merely schematic and that additional elements including other ion optical components may be provided.

According to various embodiments, a multi-dimensional survey scan may initially be performed. The multi-dimensional survey scan may comprise separating parent ions according to a first physico-chemical property (e.g. ion mobility using the ion mobility spectrometer or separator 3) and also separating the parent ions according to a second physico-chemical property (e.g. mass to charge ratio using the Time of Flight mass analyser 6).

Figure 3A:
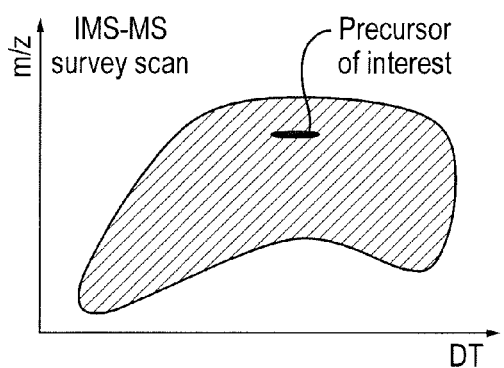
FIG. 3A shows data obtained according to an embodiment wherein an initial ion mobility-mass to charge ratio survey scan is performed and precursor or parent ions of interest are located in a single region and FIG. 3B shows data obtained according to an embodiment wherein fragmentation mass spectral data is obtained for certain ions including parent or precursor ions of interest but wherein the rest of the time further ion mobility-mass to charge ratio survey scan data is acquired.

FIG. 3A shows schematically data acquired in a multi-dimensional survey scan in accordance with an embodiment. According to this embodiment, the first physico-chemical property comprises ion mobility and the second physico-chemical property comprises mass to charge ratio. Accordingly, the x-axis of FIG. 3A represents ion mobility drift time (DT) and the y-axis represents mass to charge ratio (m/z). The shaded region shown in FIG. 3A schematically shows data acquired during the multi-dimensional survey scan.

Using the multi-dimensional survey scan, at least one parent ion of interest may be identified or determined. The determination may be made on the basis of the values of the first and second physico-chemical properties at which ions appear in the multi-dimensional survey scan and may involve evaluating the survey scan data to identify a known parent ion of interest. The parent ion of interest may, for example, be known to be present for a particular analyte or component of interest. The parent ion of interest will have a first value or range of the first physico-chemical property and a second value or range of the second physico-chemical property.

The small black region shown in FIG. 3A corresponds with a parent or precursor ion of interest e.g. a parent or precursor ion that has particular values of the first physico-chemical property (ion mobility drift time) and the second physico-chemical property (mass to charge ratio) and where it is desired to investigate the parent or precursor ions further.

After the at least one parent ion of interest has been determined, parent ions may then again be separated according the first physico-chemical property (e.g. ion mobility using ion mobility spectrometer or separator 3). The parent ions separated in this step may comprise different parent ions to the parent ions which were separated and analysed to produce the survey scan, but may have substantially the same composition (e.g. the ions may be derived from the same sample or analyte). During a single cycle of separation (e.g. during a single acquisition or experimental run) of this step the ions may also be selected (filtered) according to the second physico-chemical property (e.g. mass to charge ratio) e.g. using quadrupole mass filter 4.

It will be appreciated that a "single cycle of separation" is intended to refer to a single cycle of operation of the separator 3. Ion separators typically operate to separate ions according to a particular physico-chemical property in a periodic manner. Thus, a "single cycle of separation" for a temporal ion separator such as an ion mobility spectrometer or separator device or a Time of Flight mass analyser may comprise the time taken to separate a single sample or packet of ions while a "single cycle of separation" for a spatial ion separator may comprise a single acquisition of (mass spectral) data.

During the single cycle of separation, parent ions that correspond to the at least one parent ion of interest i.e. parent ions having substantially the first value or range of the first physico-chemical property and the second value or range of the second physico-chemical property may be selected and transmitted.

This may be done by filtering ions having substantially the first value or range of the first physico-chemical property. In an embodiment, the ions are filtered using a range of the second physico-chemical property that is based on the second value or range of the second physico-chemical property. The range of the second physico-chemical property used for filtering, may for example, be centred at the second value or range of the second physico-chemical property. In an embodiment, ions having substantially the first value or range of the first physico-chemical property within the range of the second physico-chemical property are onwardly transmitted whilst ions outside of the range of the second physico-chemical property are attenuated and/or not onwardly transmitted.

In one embodiment, this may be done by operating quadrupole mass filter 4 in a narrow band (filtering or selective) mode of operation at the appropriate time so as to filter ions having ion mobility drift time(s) corresponding to the ion mobility drift time of the at least one parent ion of interest.

In accordance with various embodiments, during the single cycle of separation, parent ions appearing at (other) values of the first physico-chemical property (e.g. parent ions that have a value or range of the first physico-chemical property that does not correspond with the second value or range) i.e. ions that do not have values of the first physico-chemical property corresponding to the at least one parent ion of interest may all be onwardly transmitted by the filter 4.

In one embodiment, this may be done by operating the quadrupole mass filter 4 in a wide band or broadband (e.g. non-filtering, non-selective or transmission) mode of operation at the appropriate time. Alternatively, this may be done by bypassing the filter 4.

It will be appreciated that in some embodiments, the filter 4, when operating in a "non-filtering" or "transmission" mode may still have a high-pass and/or a low-pass cut-off.

Thus, parent ions that appear at values or ranges of the first physico-chemical property that do not correspond to the parent ions of interest may not be filtered (e.g. are transmitted) or are filtered based on a relatively large range of the physico-chemical property e.g. that may correspond to the filter's "non-filtering" or "transmission" mode of operation. In an embodiment, ions within the relatively large range of the second physico-chemical property are onwardly transmitted. In an embodiment, the filter is operated in the mode in which it was operated to acquire the initial survey scan data at the values of the first physico-chemical property that do not correspond to parent ions of interest.

The transmitted parent ions (e.g. the parent ions that are transmitted by the filter 4), and/or one or more fragment, product or other ions derived from the transmitted parent ions may be analysed by, for example, a Time of Flight mass analyser 6. The transmitted parent ions may be fragmented or reacted in a fragmentation, reaction or collision device, such as a Collision Induced Dissociation collision cell 5,7 to produce the one or more fragment, product or other ions. It will be appreciated that embodiments in which the transmitted parent ions are fragmented or reacted effectively produce MS/MS type data.

Multiple mass spectra may be produced for the transmitted or selected parent ions and/or the fragment, product or other ions derived from the transmitted or selected parent ions. Alternatively, a single mass spectrum may be produced, e.g. for each transmitted or selected parent ion of interest, e.g. by combining data for the analysed transmitted or selected parent ions and/or fragment, product or other ions derived from the transmitted or selected parent ions. That is, a single mass spectrum may be produced for fragment ions produced from the isolated precursor ion(s) by combining data in the isolated range of the first physico chemical property.

Figure 3B:
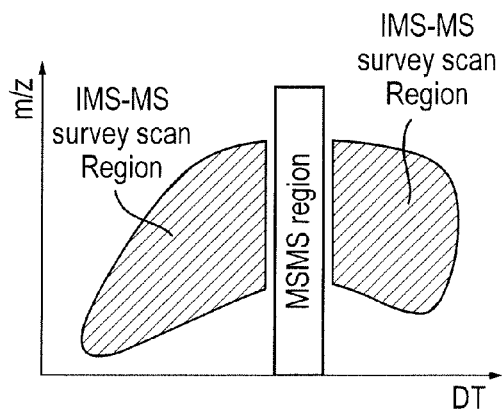

FIG. 3B shows schematically data acquired in a subsequent cycle of separation in accordance with an embodiment.

In the embodiment shown, for values of ion mobility drift time corresponding to the value of the ion mobility drift time at which the precursor ion of interest appeared in FIG. 3A, MS/MS type data is acquired for parent or precursor ions having a relatively narrow range of mass to charge ratio centred at the value of the mass to charge ratio at which the parent or precursor ion of interest appeared.

For other regions of the data (e.g. for regions of the data where no parent or precursor ions of interest are present), multidimensional (e.g. IMS-MS) survey scan type data may be acquired. In an embodiment, for these regions the parent or precursor ions are not fragmented or reacted.

In the embodiment shown in FIG. 3B the resulting data comprises three distinct regions of data namely one MS/MS region and two multidimensional survey scan regions. The two new survey scan data regions can be used in various desired ways e.g. in isolation or in conjunction with other survey scan data thereby increasing the duty cycle and speed of the instrument.

Figure 4A:
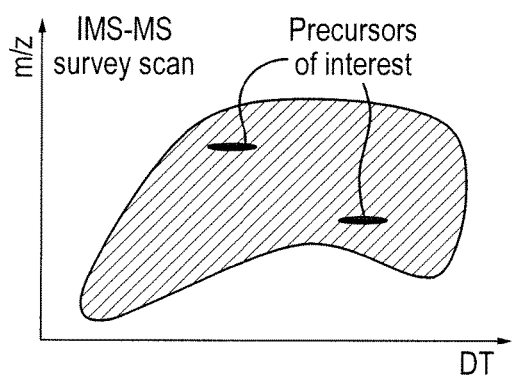
FIG. 4A shows data obtained according to an embodiment wherein an initial ion mobility-mass to charge ratio survey scan is performed and precursor or parent ions of interest are located in two regions and FIG. 4B shows data obtained according to an embodiment wherein fragmentation mass spectral data is obtained for certain ions including parent or precursor ions of interest but wherein the rest of the time further ion mobility-mass to charge ratio survey scan data is acquired.
Figure 4B:
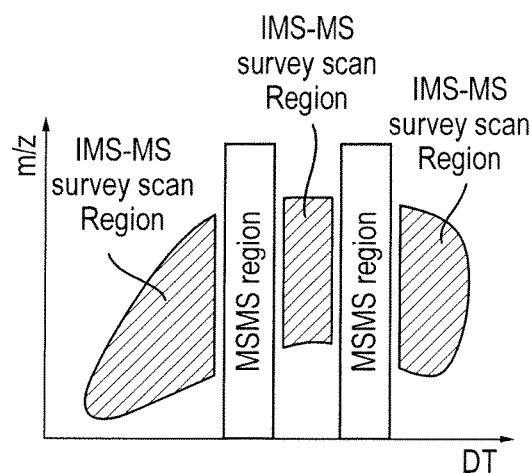

The approach can be extended to any number of precursor components of interest. FIGS. 4A and 4B show schematically data acquired in accordance with an embodiment wherein two parent or precursor components (ions) of interest are identified in an initial survey scan (FIG. 4A).

In this embodiment, in the subsequent acquisition, for values of the first physico-chemical property (ion mobility drift time) corresponding to the values of the first physico-chemical property (ion mobility drift time) at which the parent or precursor ions of interest appeared, the system is arranged to selectively transmit parent or precursor ions within relatively narrow ranges of the second physico-chemical property (mass to charge ratio) centred at the values of the second physico-chemical property (mass to charge ratio) at which the parent or precursor ions of interest appeared, and for values of the first physico-chemical property (ion mobility drift time) at which no parent or precursor ions of interest appeared, the system is arranged to non-selectively transmit parent or precursor ions i.e. to transmit parent or precursor ions having a relatively wide range of the second physico-chemical property (mass to charge ratio).

The resulting data is shown in FIG. 4B comprises five distinct regions of data namely two MS/MS regions and three multi-dimensional survey scan regions.

According to various embodiments, any number of parent or precursor components (ions) of interest can be analysed. In practice the number is limited by the resolution of the separator (e.g. ion mobility spectrometer or separator 3) and the speed at which the individual parent or precursor components can be isolated (e.g. by a quadrupole mass filter 4).

It should be noted that although the figures show the MS/MS data regions as being "vertical" (i.e. appearing across the entire y-range for a given range in the x-direction), in practice the region may appear to be curved, depending on instrument geometries. This is because ions (e.g. parent or precursor and/or fragment ions) may continue to separate (or may lose separation) as they traverse downstream devices such as gas filled RF ion guides and/or ion focusing optics etc.

In an embodiment, an apparatus for IMS-MS is provided comprising an ion mobility spectrometer or separator ("IMS") device arranged upstream of a mass to charge ratio filter and a mass analyser. The mass to charge ratio filter may be arranged to switch between a wide band or broadband transmission mode of operation and a mass to charge ratio filtering mode of operation within an ion mobility separation (IMS) cycle. The switching may be driven by a survey scan, in an embodiment a multi-dimensional survey scan. The switching may occur more than once within the ion mobility separation (IMS) cycle.

In an embodiment, the different mass to charge ratio-ion mobility drift time regions associated with the switches are stored as separate spectra. In an embodiment, multiple mass to charge ratio-ion mobility drift time experiments are combined for the same parent or precursor ions.

Embodiments extend to arrangements in which the first physico-chemical property is something other than ion mobility and the (first) separator comprises a device other than an ion mobility spectrometer or separator 3. The first physico-chemical property may comprise, for example, mass to charge ratio. In such embodiments, the (first) separator may comprise a device that separates ions according to mass to charge ratio as a function of time. Examples of such separators include ion traps and scanning mass to charge ratio filters.

Figure 5A:
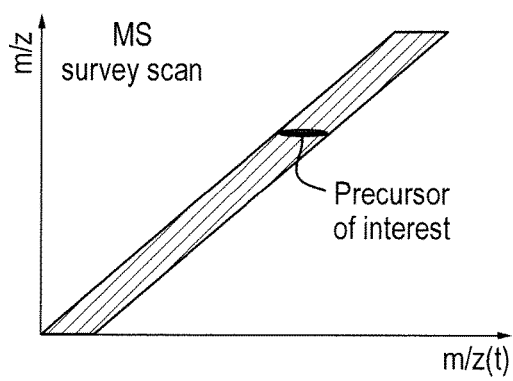
FIG. 5A shows data obtained according to an embodiment wherein an initial mass to charge ratio survey scan is performed and precursor or parent ions of interest are located in a single region and FIG. 5B shows data obtained according to an embodiment wherein fragmentation mass spectral data is obtained for certain ions including parent or precursor ions of interest but wherein the rest of the time ion mobility-mass to charge ratio survey scan data is acquired.
Figure 5B:
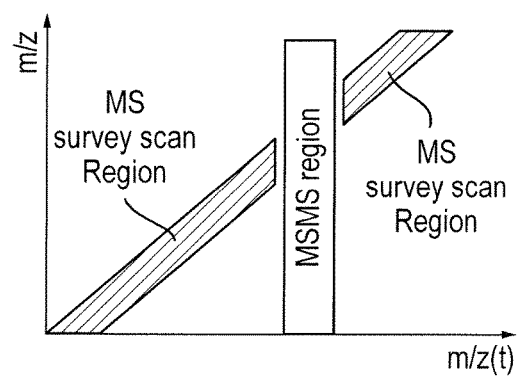

FIGS. 5A and 5B show schematically data acquired in accordance with an embodiment wherein both the first and second physico-chemical properties comprise mass to charge ratio. One or more parent or precursor ions of interest may be identified in the survey scan data (FIG. 5A). In the subsequent analysis (FIG. 5B), the parent or precursor ions of interest may be isolated (selected) and subjected to MS/MS analysis (i.e. the parent or precursor ions are fragmented or reacted so as to produce fragment or product ions, and the resulting fragment or product ions may be analysed), while other regions of the data may be subjected to a multi-dimensional survey scan analysis.

In various embodiments, mass to charge ratio filtering may be achieved in any suitable and desired manner, such as using a quadrupole mass filter or using resonant ejection notches in quadrupole devices.

According to various embodiments the additional multi-dimensional survey scan data may be collapsed into a single dimension for interrogation.

The isolation region may cut across the temporal profile of a non-selected eluting ion mobility (IMS) peak and, as such, the resultant new survey scan data may be rescaled to account for this effect.

Embodiments may be combined with other ion mobility separation and Time of Flight techniques. In one embodiment the techniques of the various embodiments may be combined with linked quadrupole low mass cut off scans synchronised with ion mobility separation cycle time in manner substantially as described in U.S. Pat. No. 7,586,088 (Micromass) e.g. for charge state selection of survey scan data. In another embodiment, enhanced Time of Flight operation modes such as Enhanced Duty Cycle ("EDC") and/or High Duty Cycle ("HDC") may be used.

In various embodiments, spatially distributed or parallel filters may be used, optionally together with mass to charge ratio dependent diverters and/or delay lines. In these embodiments data regions containing parent or precursor ions of interest (mass to charge ratio range(s)) at a given drift time may be removed (and in an embodiment fragmented and/or analysed) whilst allowing the remaining mass to charge ratio ranges to be onwardly transmitted and remain part of the IMS-MS survey scan.

It can be seen from the above that the various embodiments provide an improved method of analysing ions, method of mass spectrometer, ion analyser and mass spectrometer having an improved duty cycle for Data Dependent Acquisition ("DDA") type experiments.

Although the present invention has been described with reference to preferred embodiments, it will be understood by those skilled in the art that various changes in form and detail may be made without departing from the scope of the invention as set forth in the accompanying claims.

The invention claimed is:

1. A method of analysing ions comprising:
performing an initial multi-dimensional survey scan comprising separating parent ions according to a first physico-chemical property and separating said parent ions according to a second physico-chemical property;
determining at least one parent ion of interest from said initial multi-dimensional survey scan, said at least one parent ion of interest having a first value or range of said first physico-chemical property and a second value or range of said second physico-chemical property;
and then during a subsequent single cycle of separation:
(i) separating parent ions according to said first physico-chemical property;
wherein if said parent ions have a value or range of said first physico-chemical property which corresponds with said first value or range, then said method further comprises selecting parent ions of interest having a value or range of said first physico-chemical property which corresponds with said first value or range and which also have a value or range of said second physico-chemical property which corresponds with said second value or range; and
wherein if said parent ions have a value or range of said first physico-chemical property which does not correspond with said first value or range then said method further comprises separating said parent ions according to said first physico-chemical property and separating said parent ions according to said second physico-chemical property.

2. A method as claimed in claim 1, wherein said first physico-chemical property comprises ion mobility, differential ion mobility, mass, mass to charge ratio or time of flight.

3. A method as claimed in claim 1, wherein said second physico-chemical property comprises ion mobility, differential ion mobility, mass, mass to charge ratio or time of flight.

4. A method as claimed in any claim 1, wherein separating ions according to said first physico-chemical property comprises separating ions temporally.

5. A method as claimed in claim 1, wherein separating ions according to said second physico-chemical property comprises separating ions temporally.

6. A method as claimed in claim 1, wherein separating ions according to said first physico-chemical property comprises separating ions spatially.

7. A method as claimed in claim 1, wherein separating ions according to said second physico-chemical property comprises separating ions spatially.

8. A method as claimed in claim 1, further comprising using an ion mobility or differential ion mobility separator to separate said parent ions according to their ion mobility or differential ion mobility.

9. A method as claimed in claim 1, further comprising using a time of flight mass analyser, an ion trap or a scanning mass to charge ratio filter to separate said parent ions according to their mass, mass to charge ratio or time of flight.

10. A method as claimed in claim 1, further comprising using a quadrupole rod set mass filter or a notched broadband quadrupolar frequency to filter said parent ions according to their mass, mass to charge ratio or time of flight.

11. A method as claimed in claim 1, further comprising causing said selected parent ions of interest to fragment or react so as to form fragment or product ions.

12. A method as claimed in claim 1, wherein said first physico-chemical property and said second physico-chemical property are substantially correlated.

13. A method as claimed in claim 1, wherein said first physico-chemical property and said second physico-chemical property are substantially different and/or are substantially uncorrelated.

14. A method as claimed in claim 1, wherein said method comprises:
determining at least a first parent ion of interest and a second parent ion of interest from said initial multi-dimensional survey scan, said first parent ion of interest having a first value or range of said first physico-chemical property and a second value or range of said second physico-chemical property, said second parent ion of interest having a third value or range of said first physico-chemical property and a fourth value or range of said second physico-chemical property;
and then during said subsequent single cycle of separation:
(i) separating parent ions according to said first physico-chemical property;
wherein if said parent ions have a value or range of said first physico-chemical property which corresponds with said first value or range, then said method further comprises selecting parent ions of interest having a value or range of said first physico-chemical property which corresponds with said first value or range and which also have a value or range of said second physico-chemical property which corresponds with said second value or range;

wherein if said parent ions have a value or range of said first physico-chemical property which corresponds with said third value or range, then said method further comprises selecting parent ions of interest having a value or range of said first physico-chemical property which corresponds with said third value or range and which also have a value or range of said second physico-chemical property which corresponds with said fourth value or range; and wherein if said parent ions have a value or range of said first physico-chemical property which does not correspond with said first and/or third value or range then said method further comprises separating said parent ions according to said first physico-chemical property and separating said parent ions according to said second physico-chemical property.

15. An analytical instrument for analysing ions comprising:
a first separator for separating ions according to a first physico-chemical property;
a second separator for separating ions according to a second physico-chemical property; and
a control system arranged and adapted:
(i) to perform an initial multi-dimensional survey scan comprising separating parent ions according to said first physico-chemical property using said first separator and separating said parent ions according to said second physico-chemical property using said second separator;
(ii) to determine at least one parent ion of interest from said initial multi-dimensional survey scan, said at least one parent ion of interest having a first value or range of said first physico-chemical property and a second value or range of said second physico-chemical property;
and then during a single cycle of separation:
(iii) to cause said first separator to separate parent ions according to said first physico-chemical property;
(iv) if said parent ions have a value or range of said first physico-chemical property which corresponds with said first value or range, to select parent ions of interest having a value or range of said first physico-chemical property which corresponds with said first value or range and which also have a value or range of said second physico-chemical property which corresponds with said second value or range; and (v) if said parent ions have a value or range of said first physico-chemical property which does not correspond with said first value or range, to separate said parent ions according to said first physico-chemical property using said first separator and to separate said parent ions according to said second physico-chemical property using said second separator.

16. A method of analysing ions comprising:
performing an initial multi-dimensional survey scan comprising separating parent ions according to a first physico-chemical property and separating said parent ions according to a second physico-chemical property;
determining at least one parent ion of interest from said initial multi-dimensional survey scan, said at least one parent ion of interest having a first value or range of said first physico-chemical property and a second value or range of said second physico-chemical property; and then
separating parent ions according to said first physico-chemical property in a single cycle of separation, and during said single cycle of separation:
fragmenting or reacting parent ions having a value or range of said first physico-chemical property corresponding to said first value or range and having a value or range of said second physico-chemical property corresponding to said second value or range of said second physico-chemical property so as to form fragment or product ions, and analysing said fragment or product ions; and
analysing parent ions having a value or range of said first physico-chemical property that does not correspond with said first value or range.

17. A method of mass spectrometry comprising a method as claimed in claim 1.

18. A mass spectrometer comprising an analytical instrument as claimed in claim 15.

19. A method as claimed in claim 1, wherein said first physico-chemical property and said second physico-chemical property are the same.

20. A method of mass spectrometry comprising a method as claimed in claim 16.

* * * * *